United States Patent
Miles et al.

(10) Patent No.: US 7,901,623 B2
(45) Date of Patent: Mar. 8, 2011

(54) LATERAL FLOW STRIP ASSAY

(75) Inventors: Robin R. Miles, Danville, CA (US); William J. Benett, Livermore, CA (US); Matthew A. Coleman, Oakland, CA (US); Francesca S. Pearson, Livermore, CA (US); Shanavaz L. Nasarabadi, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 720 days.

(21) Appl. No.: 11/528,286

(22) Filed: Sep. 26, 2006

(65) Prior Publication Data

US 2008/0076169 A1   Mar. 27, 2008

(51) Int. Cl.
*G01N 33/00* (2006.01)

(52) U.S. Cl. ............... 422/58; 436/164; 436/169; 435/4; 435/287.1; 422/50; 422/55; 422/61; 422/68.1; 422/104

(58) Field of Classification Search ............ 422/50, 422/55, 58, 61, 68.1, 104; 435/4, 287.1; 436/164, 169
See application file for complete search history.

(56) References Cited

U.S. PATENT DOCUMENTS

| 5,147,608 | A | 9/1992 | Hudson et al. |
| 6,303,081 | B1 * | 10/2001 | Mink et al. ....................... 422/61 |
| 6,375,896 | B1 * | 4/2002 | Wuske et al. .................... 422/58 |
| 7,156,658 | B2 * | 1/2007 | Shoup ............................. 433/72 |
| 2002/0173047 | A1 * | 11/2002 | Hudak et al. ................. 436/178 |
| 2003/0027352 | A1 | 2/2003 | Hooper et al. |
| 2004/0171173 | A1 * | 9/2004 | Eckermann et al. ......... 436/514 |
| 2005/0175992 | A1 * | 8/2005 | Aberl et al. ....................... 435/5 |
| 2005/0227371 | A1 | 10/2005 | Gokhan |
| 2006/0018800 | A1 * | 1/2006 | Slowey et al. ................ 422/102 |

FOREIGN PATENT DOCUMENTS

EP       0 384 504 A1    8/1990

* cited by examiner

*Primary Examiner* — Melanie J Yu
(74) *Attorney, Agent, or Firm* — Eddie E. Scott; James S. Tak

(57) ABSTRACT

A lateral flow strip assay apparatus comprising a housing; a lateral flow strip in the housing, the lateral flow strip having a receiving portion; a sample collection unit; and a reagent reservoir. Saliva and/or buccal cells are collected from an individual using the sample collection unit. The sample collection unit is immersed in the reagent reservoir. The tip of the lateral flow strip is immersed in the reservoir and the reagent/sample mixture wicks up into the lateral flow strip to perform the assay.

3 Claims, 6 Drawing Sheets

LATERAL FLOW STRIP ASSAY

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to assay and more particularly to lateral flow strip assay.

2. State of Technology

United States Published Patent Application No. 2005/0227371 by Cem Gokhan for a hybrid phase lateral flow assay, assigned to Quidel Corporation, provides the following state of technology information:

"Lateral-flow immunoassays, with their ease of use, speed and reliability, are widely used for self-testing and in the clinical setting. Lateral-flow immunoassays are probably the most common non-electrical method used in rapid medical diagnostics to detect the presence of a specific analyte in a liquid sample.

In the general method, a liquid sample suspected of containing the analyte is applied to a porous carrier. Different porous materials are commonly used for the porous carrier, and can differ in pore size, flow rate, protein-binding specifications and pre-treatment, etc. Essentially, all of the physical activities (e.g., liquid migration) and chemical reactions take place in the porous carrier, in the following order.

First a liquid sample to be tested is introduced to a designated area in the sampling-end (also referred as the 'proximal end' or 'wet end') of the porous carrier, for a measured time e.g. 5 seconds or in a measured volume e.g. 2 drops. From this point forward, the liquid sample migrates within the porous carrier to the direction of the dry end (also referred as the 'distal end'). At the outset of the migration, the liquid sample is frequently optimized for reaction by means of chemicals e.g. pH agents or buffers, surfactants, and/or blockers impregnated into the porous carrier.

Second, while migrating in the porous carrier, the sample mobilizes a labeled reagent that has been reversibly (temporarily) immobilized in the porous carrier. The zone where the mobilizable labeled reagent is located is often referred to as the 'labeling zone,' but can be referred to as the 'reversible immobilization zone' or 'mobilization zone'—the terms are equivalent.

Third, while analyte is reacting with the mobilized labeled reagent, the liquid sample and mobilized labeled reagent migrates further within the porous carrier to the detection zone, (which may also be referred to the 'irreversible immobilization zone' or merely the 'immobilization zone') where reagent that binds the same analyte is fixed or immobilized, usually in the form of a line. When analyte is present in the liquid sample, a 'sandwich' in the form of the mobilized labeled reagent:analyte:immobilized reagent is formed, and the resulting concentration of the labeled reagent leads to a visible line appearing in the detection zone, which is indicative of a positive result.

Lastly, remaining sample liquid, together with the rest of the labeled reagent further migrates to a control zone, where a second line appears indicating that sample has progressed through the detection and control zones and that the assay has provided a valid test result. The rest of the sample and the remaining labeled reagent then migrate to a porous sink. Labeled reagent remaining in the porous carrier (other than in the detection zone, control zone or sink) makes up any background signal. In some instances where the migration direction reverses, so called 'back flow,' occurs. Furthermore, the porous carrier can be pre-treated with chemicals e.g. surfactants.

Lateral-flow immunoassays can also function on the basis of competitive binding of the analyte. In these devices, lack of the test line generally indicates a positive result.

The most common example of a lateral-flow immunoassay device is a pregnancy test. These devices are commonly provided for home use, in a plastic housing with a fibrous or a porous extension, which can be held to a urine stream to collect urine sample into the housing. The urine sample collected this way then migrates to the porous carrier, which contains the labeled reagent and the series of events mentioned above starts. The analyte detected in a pregnancy test is Human Chorionic Gonadotropin (hCG) and the reagents commonly used are anti-hCG monoclonal or polyclonal antibodies. The most common labels are gold or latex particles.

Another known example of a lateral-flow immunoassay device commonly provided for home use is an ovulation test, the analyte being Luteinizing Hormone (LH) and reagents being anti-LH, and the rest of the device being similar to a pregnancy test.

A professional format of lateral-flow immunoassay devices commonly referred to as cassette tests, have smaller housings and a sample application orifice instead of the fibrous extension. The sample orifice exposes part of the porous carrier where a liquid sample can be dispensed with a pipette, directly to the porous carrier."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention was developed as part a project to develop suitable protein markers in saliva/buccal cells to indicate exposure to radiation and to then to develop a triage device for testing for the presence of these markers. Potential victims of a terrorist radiological event will express certain proteins indicative of radiation exposure. Saliva/buccal cells can be collected fairly readily by minimally trained personnel using the present invention and analyzed for the expression of these proteins. This provides for quick, inexpensive testing of large numbers of affected individuals.

The present invention provides a lateral flow strip assay apparatus comprising a housing; a lateral flow strip in the housing, the lateral flow strip having a receiving portion; a sample collection unit; and a reagent reservoir. The present invention works by first collecting saliva and/or buccal cells from an individual using the sample collection unit then immersing the sample collection unit into the reagent reservoir, then extracting the sample collection unit from the reservoir. Then the tip of the lateral flow strip is immersed in the reservoir and the reagent/sample mixture wicks up into the lateral flow strip to perform the assay. The sample collection unit consists of a swab, cytobrush, spatula, or a sponge for collecting buccal cells and saliva. The reservoir contains a reagent mixture which is used to wash the material from the sample collection unit. The reagent mixture can contain lysing solution to help extract proteins from the buccal cells. The solution can also be used to reduce the viscosity of the saliva sample to make the lateral flow assay proceed more rapidly. In one embodiment, the entrance to the reagent reservoir is tapered into an hour-glass shape such that a sponge collector can be squeezed while retracting the sponge from the reservoir to increase the volume of sample introduced into the reservoir. The sponge can be squeezed in the process of insertion into the reservoir to aid in mixing the sample. Sufficient height above the restriction prevents overflow of the sample. The reservoir can be sealed prior to use using a cap, a sealed lid or a septum.

The tip of the lateral flow strip which is housed in the housing protrudes slightly from the housing. This tip is immersed in the sample-regent reservoir following introduction of the sample into the reservoir. The liquid is wicked up the lateral flow strip due to capillary forces. Flanges in the housing prevent the tip from being immersed too far into the reservoir. In one embodiment, a viewing window in the housing permits easy reading of the lateral flow assay results.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
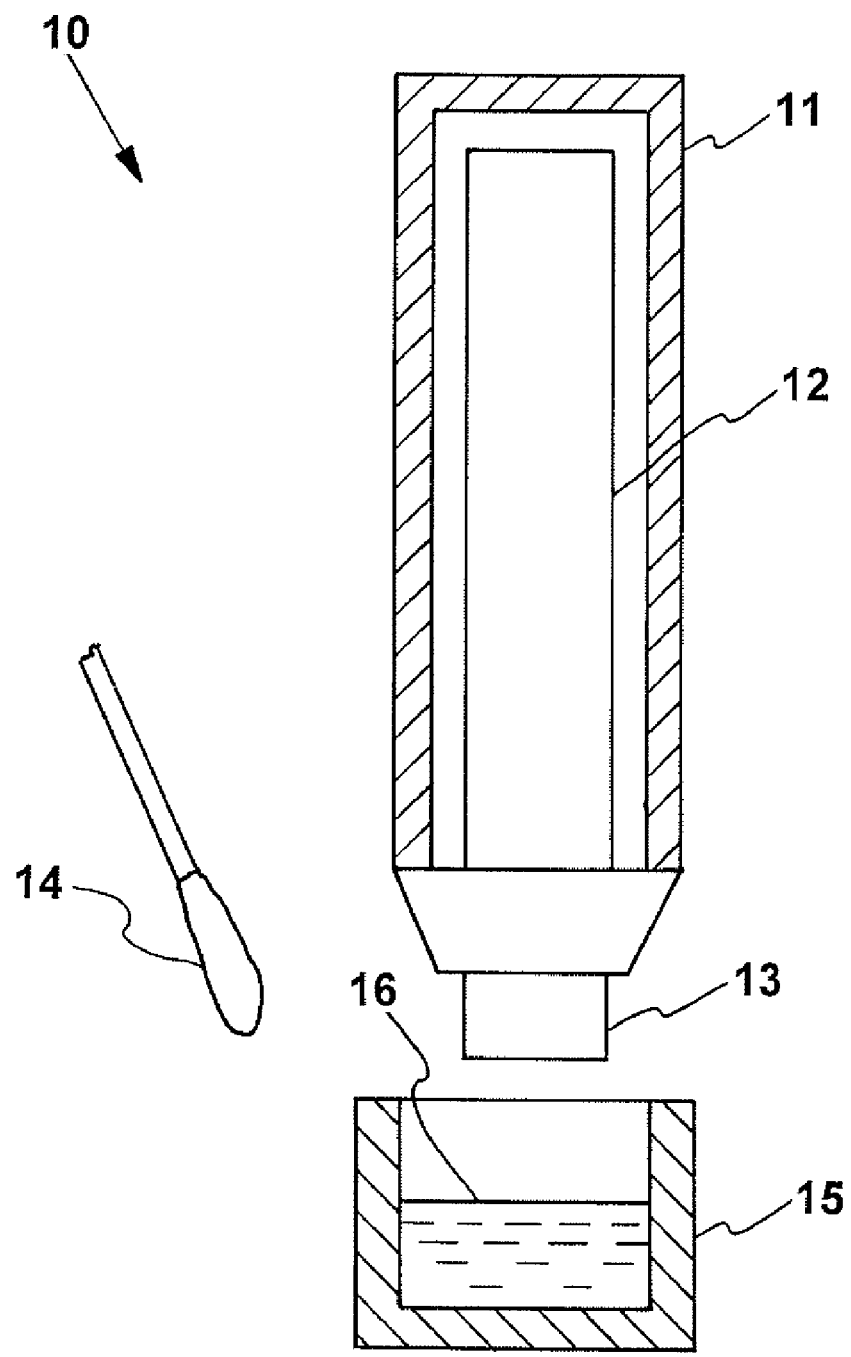
FIG. 1 illustrates one embodiment of a system constructed in accordance with the present invention.

Referring to the drawings, to the following detailed description, and to incorporated materials, detailed information about the invention is provided including the description of specific-embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings, and in particular to FIG. 1, one embodiment of a system constructed in accordance with the present invention is illustrated. This embodiment of the present invention is designated generally by the reference numeral 10.

The system 10 is a lateral flow strip assay device. The device 10 is a simple-to-use sample collection and processing package for lateral flow strip assays. The device includes a lateral flow strip housing 11 with a lateral flow strip 12 in the housing 11. The lateral flow strip 12 has a receiving portion 13 that extends from the lateral flow strip housing 11. The system 10 includes a sample collection unit 14 and a reagent reservoir 15 containing a reagent 16.

The lateral flow strip 12 is a later flow strip such as that described in Published United States Patent Application No. 2005/0227371 by Cem Gokhan, assigned to Quidel Corporation, for a hybrid phase lateral flow assay, or later flow strips commercially available. The disclosure of Published United States Patent Application No. 2005/0227371 by Cem Gokhan, assigned to Quidel Corporation, for a hybrid phase lateral flow assay is incorporated herein by this reference.

The system 10 works by first collecting sample cells from an individual using the sample collection unit 14 then immersing the sample collection unit 14 into the reagent reservoir 15 then extracting the sample collection unit 14 from the reservoir 15 then immersing the receiving portion 13 of the lateral flow strip 12 into the reservoir 15. The reagent 16 and sample mixture wicks up the lateral flow strip 12 to perform the assay. The lateral flow strip 12 operates whereby the sample is applied at the end 13 and flows through the flow strip 12 matrix, binding with secondary and primary constituents that have been applied to the flow strip 12 during the manufacturing process.

The system 10 can be used to interrogate saliva for protein or RNA markers to determine the state of the person or animal being assayed. In particular, this device was developed for indications of radiological exposure by testing for the presence of certain proteins associated with exposure. The system 10 has use for markers for drug use or illness. Health officials can use the system 10 to detect illness in patients using appropriate markers in saliva, buccal, or other cells. Law enforcement personal can use the system 10 for drug use.

Figure 2:
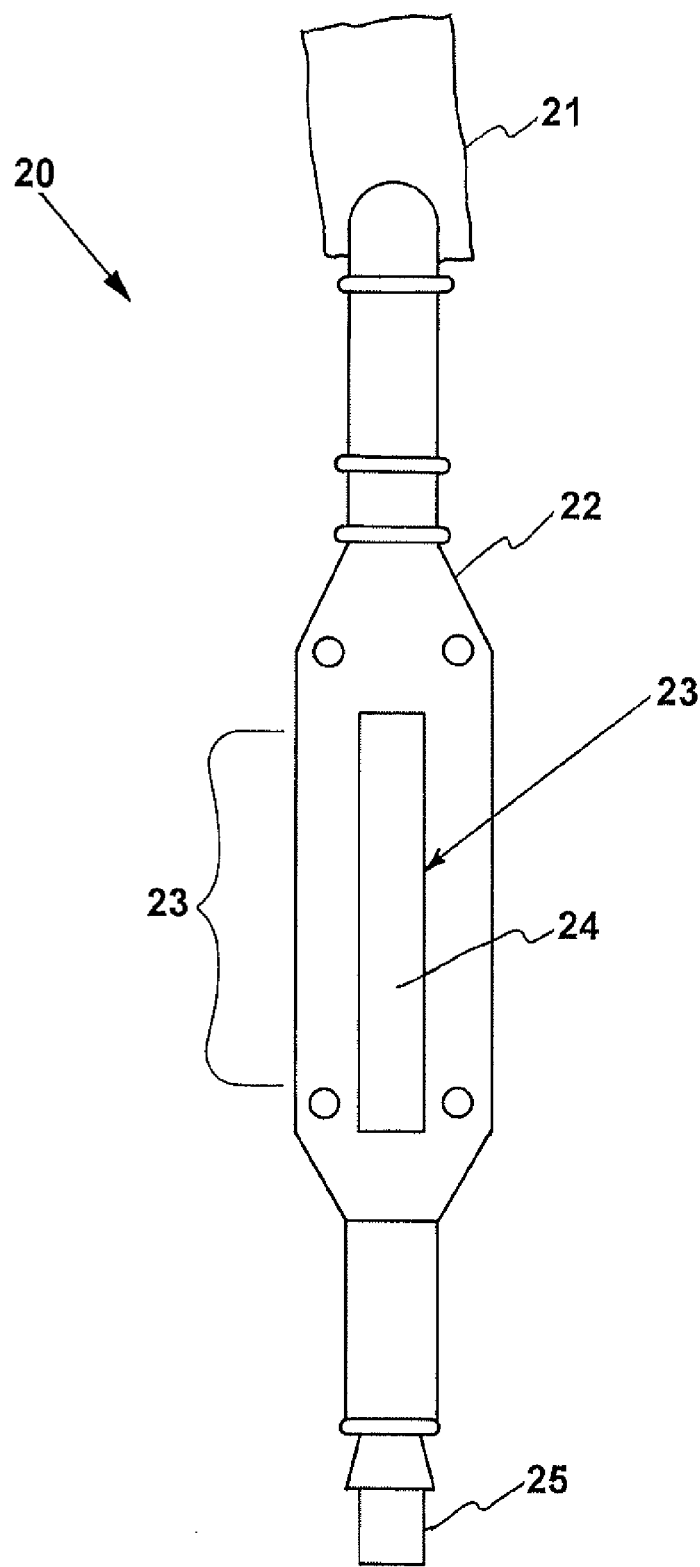
FIG. 2 shows a rod-like platform one end of which is used to collect a sample and the other end of which houses a lateral flow strip.
Figure 3:
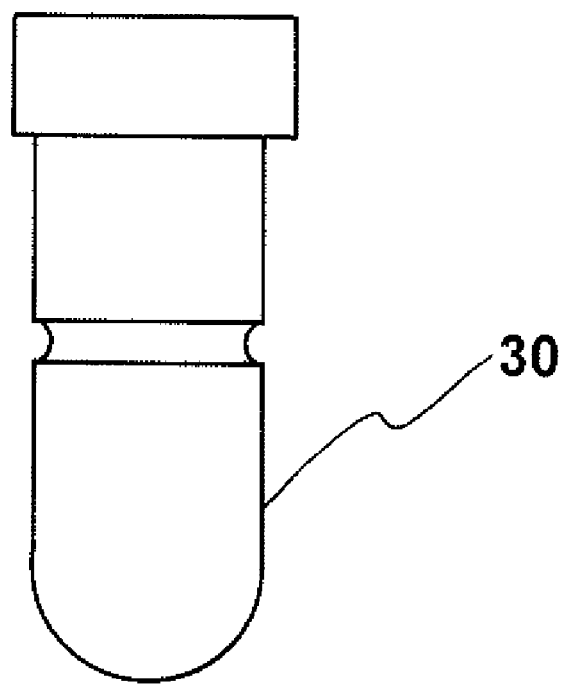
FIG. 3 shows a reagent container.
Figure 4:
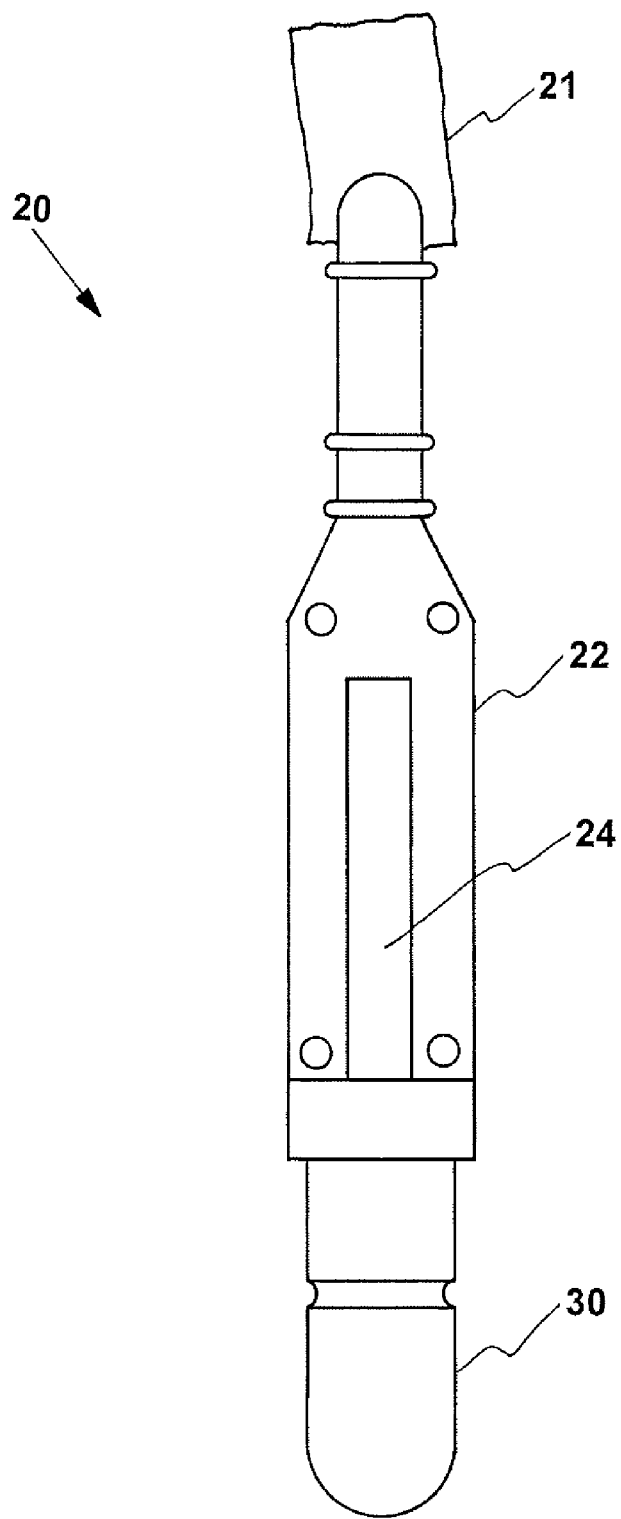
FIG. 4 shows the lateral flow strip immersed into the reservoir to allow the reagent/sample mixture to wick up the lateral flow strip to perform the assay.

Referring now to FIGS. 2, 3, and 4, another embodiment of a system constructed in accordance with the present invention is illustrated. This embodiment of the present invention is designated generally by the reference numeral 20.

The system 20 is a lateral flow strip assay device. The device 20 is a simple-to-use sample collection and processing package for lateral flow strip assays. The system 20 has two parts, a rod-like platform 22 one end 21 of which is used to collect the sample and the other end of which houses the lateral flow strip 24, and a reagent container 30 which is used to remove sample from the collection tip 21 and introduce sample to the lateral flow strip 24 for analysis. The end 25 of the lateral flow strip 24 extends from the rod-like platform 22. The rod-like platform 22 includes a viewing window 23.

The system 20 can be used to interrogate saliva for protein or RNA markers to determine the state of the person or animal being assayed. In particular, the system 20 was developed for indications of radiological exposure by testing for the presence of certain proteins associated with exposure. The system 20 was developed as part of a project to develop suitable protein markers in saliva/buccal cell to indicate exposure to radiation and to then to develop a triage device for testing for the presence of these markers. Potential victims of a terrorist radiological event will express certain proteins indicative of radiation exposure. Saliva/buccal cells can be collected fairly readily by minimally trained personnel using the system 20 and analyzed for the expression of these proteins. This provides for quick, inexpensive testing of large numbers of affected individuals.

The lateral flow strip 24 is a lateral flow strip this currently available and is used for biological tests. The most common application is the home pregnancy test. Use of these strips for chemical tests in saliva is well known. The system 20 is a simple dual ended package, one end 21 for sample collection and the other end to house the lateral flow strip 24, and a separate reagent reservoir 30 to condition the sample. The end 25 of the lateral flow strip 24 extends from the end of the housing 22. The user simply sequentially places each end 21 and 25 into the reagent reservoir 30 after taking the sample.

The system 20 works by first collecting saliva and/or buccal cells from an individual using the sample collection component 21 then immersing the sample collection component 21 into the reagent reservoir 30, then extracting the sample collection component 21 from the reservoir 30, then turning the rod-platform 22 around (180 degrees) so that the tip 25 of the lateral flow strip 22 is then immersed into the reservoir 30 and the reagent/sample mixture wicks up into the strip 24 to perform the assay as shown in FIG. 4. The sample collection component 21 consists of a swab, cytobrush or spatula for collecting buccal cells or a sponge as pictured in FIG. 2 for collecting both buccal cells and saliva.

The reservoir 30 contains a reagent mixture which is used to wash the material from the sample collection component 21. The reagent mixture can contain lysing solution to help extract proteins from the buccal cells. The solution can also be used to reduce the viscosity of the saliva sample to make the lateral flow assay proceed more rapidly. The entrance to the reagent reservoir 30 is tapered into an hour-glass shape such that a sponge collector can be squeezed while retracting the sponge from the reservoir to increase the volume of sample introduced into the reservoir. The sponge can be squeezed in the process of insertion into the reservoir to aid in mixing the sample. Sufficient height above the restriction prevents overflow of the sample. The reservoir can be sealed prior to use using a cap, a sealed lid or a septum.

The tip 25 of the lateral flow strip 24 which is housed in the rod-like structure 22 protrudes slightly from the housing 22. This tip 25 is immersed in the sample-regent reservoir 30 following introduction of the sample into the reservoir 30 as shown in FIG. 4. The liquid is wicked up the lateral flow strip 24 due to capillary forces. Flanges in the housing prevent the tip from being immersed too far into the reservoir. The viewing window 23 in the housing 22 permits easy reading of the lateral flow assay results.

Figure 5B:
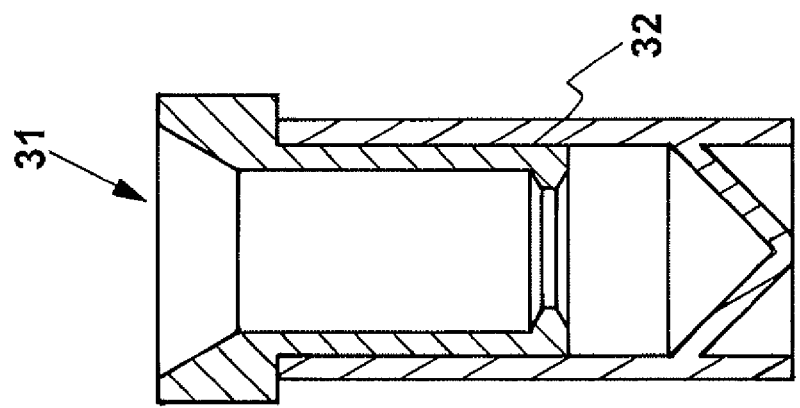
FIGS. 5A and 5B show the entrance to the reagent reservoir in greater detail.
Figure 5A:
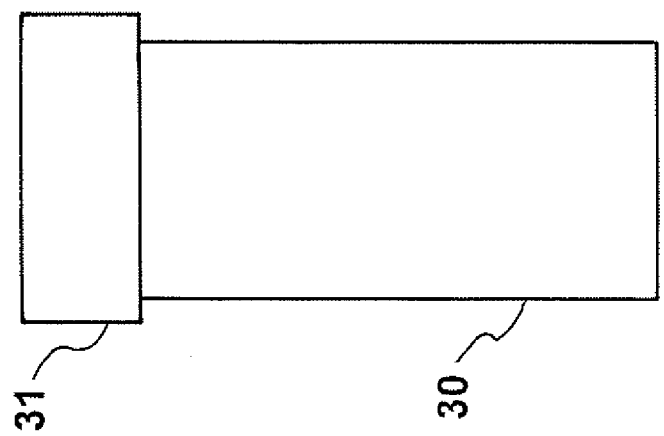

Referring now to FIGS. 5A and 5B, the entrance to the reagent reservoir 30 is shown in greater detail. The entrance 31 to the reagent reservoir 30 is tapered into an hour-glass shape 32 as shown in FIGS. 5A and 5B such that a sponge collector can be squeezed while retracting the sponge from the reservoir to increase the volume of sample introduced into the reservoir. The sponge can be squeezed in the process of insertion into the reservoir to aid in mixing the sample. Sufficient height above the restriction prevents overflow of the sample. The reservoir can be sealed prior, to use using a cap, a sealed lid or a septum.

Figure 6:
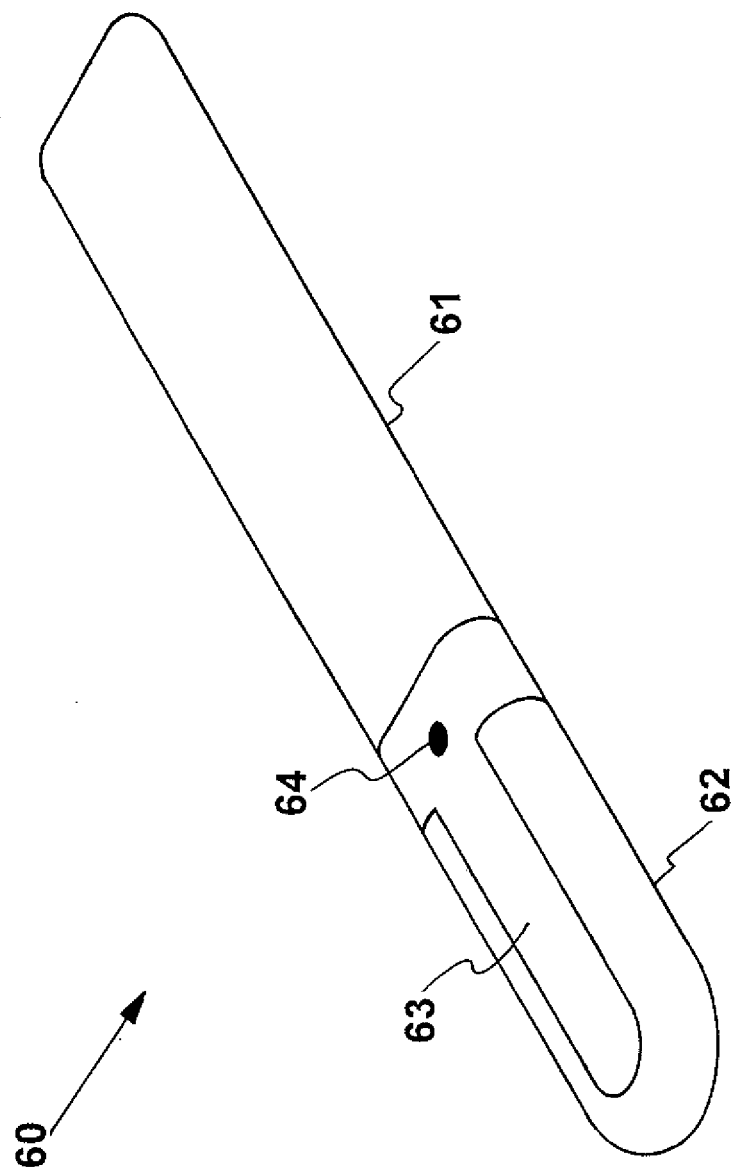
FIG. 6 shows a rubber chewbar that enhances sample collection.

Referring now to FIG. 6, another embodiment of a system constructed in accordance with the present invention is illustrated. This embodiment of the present invention is designated generally by the reference numeral 60.

The system 60 is a lateral flow strip assay device. The device 60 is a simple-to-use sample collection and processing package for lateral flow strip assays. The system 60 includes a lateral flow strip housing 61 with a lateral flow strip in the housing 61.

The system 60 includes a rubber chew bar 62 that enhances sample collection. In the system 60 the sample collection unit consists of the rubberized chew bar 62 surrounding the sponge 63. A colorimetric humidity indicator 64 is incorporated into the unit. As the subject chews on the chew bar 62 and saliva is absorbed into the sponge 63 the indicator will change color as water is absorbed indicating sufficient sample collection.

The system 60 works by first collecting sample cells from an individual using the sample collection unit then immersing the sample collection unit into a reagent reservoir then extracting the sample collection unit from the reservoir then immersing the receiving portion of the lateral flow strip into the reservoir. The reagent and sample mixture wicks up the lateral flow strip to perform the assay.

The system 60 can be used to interrogate saliva for protein or RNA markers to determine the state of the person or animal being assayed. In particular, this device was developed for indications of radiological exposure by testing for the presence of certain proteins associated with exposure. The system 60 has use for markers for drug use or illness. Health officials can use the system 60 to detect illness in patients using appropriate markers in saliva, buccal, or other cells. Law enforcement personal can use the system 60 for drug use.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A lateral flow strip assay apparatus for testing a sample, comprising:
    a housing, said housing having an end portion;
    a lateral flow strip, said lateral flow strip positioned in said housing, said lateral flow strip having a tip with a receiving portion on said tip with said tip of said lateral flow strip extending outside of said housing from said end portion of said housing;
    a sample collection unit for collecting the sample; and
    a reagent reservoir for receiving said tip of said lateral flow strip, wherein said reagent reservoir includes an entrance for receiving said sample collection unit and a tapered portion for squeezing said sample collection unit.

2. A lateral flow strip assay apparatus of for testing a sample, comprising:
    a housing having a first end portion and a second end portion;
    a lateral flow strip, said lateral flow strip positioned in said housing, said lateral flow strip having a tip with a receiving portion on said tip with said tip of said lateral flow strip extending from said first end portion of said housing;
    a sample collection unit for collecting the sample, said sample collection unit connected to said second end portion of said housing; and
    a reagent reservoir for receiving said tip of said lateral flow strip, wherein said reagent reservoir includes an entrance for receiving said sample collection unit and a tapered portion for squeezing said sample collection unit.

3. A lateral flow strip assay apparatus for testing a sample, comprising:
   a housing having an upper end and a lower end;
   a lateral flow strip, said lateral flow strip positioned in said housing, said lateral flow strip having a tip with a receiving portion on said tip with said tip of said lateral flow strip extending from said lower end of said housing;
   a window in said housing for viewing said lateral flow strip;
   a sample collection unit for collecting the sample, said sample collection unit connected to said upper end of said housing; and
   a reagent reservoir for receiving said tip of said lateral flow strip, wherein said reagent reservoir includes an entrance for receiving said sample collection unit and a tapered portion for squeezing said sample collection unit.

* * * * *